(12) United States Patent
Amit (10) Patent No.: US 11,481,909 B2
(45) Date of Patent: Oct. 25, 2022

(54) METHOD AND APPARATUS FOR PERFORMING FACIAL REGISTRATION

(71) Applicant: BIOSENSE WEBSTER (ISRAEL) LTD., Yokneam (IL)

(72) Inventor: Matityahu Amit, Cohav-Yair Zur-Yigal (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 16/212,060

(22) Filed: Dec. 6, 2018

(65) Prior Publication Data

US 2020/0184661 A1 Jun. 11, 2020

(51) Int. Cl.
*G06T 7/33* (2017.01)
*G06T 7/00* (2017.01)
*G06V 40/16* (2022.01)

(52) U.S. Cl.
CPC .............. *G06T 7/337* (2017.01); *G06T 7/97* (2017.01); *G06V 40/172* (2022.01); *G06T 2207/10081* (2013.01); *G06T 2207/30201* (2013.01)

(58) Field of Classification Search
None
See application file for complete search history.

(56) References Cited

U.S. PATENT DOCUMENTS

| | | | |
|---|---|---|---|
| 5,464,144 A | 11/1995 | Guy et al. | |
| 6,139,214 A | 10/2000 | Zirps et al. | |
| 6,312,434 B1 * | 11/2001 | Sutrina | A61B 17/22012 606/127 |
| 10,751,509 B2 * | 8/2020 | Misener | A61B 5/061 |
| 2002/0184122 A1 | 12/2002 | Yamaguchi et al. | |
| 2006/0073728 A1 | 4/2006 | Zaiken et al. | |
| 2007/0208252 A1 | 9/2007 | Makower | |
| 2008/0044104 A1 | 2/2008 | Gering | |
| 2008/0152205 A1 | 6/2008 | Vaillant et al. | |
| 2012/0245760 A1 * | 9/2012 | Ikeya | B60R 1/00 701/1 |
| 2014/0188133 A1 * | 7/2014 | Misener | A61B 8/0833 606/130 |
| 2017/0020411 A1 | 1/2017 | Gliner et al. | |
| 2018/0325610 A1 * | 11/2018 | Cameron | G06T 7/74 |
| 2019/0192228 A1 * | 6/2019 | Salazar | A61B 34/20 |
| 2020/0054399 A1 * | 2/2020 | Duindam | A61B 34/10 |

FOREIGN PATENT DOCUMENTS

EP 3292835 A1 3/2018

OTHER PUBLICATIONS

Extended European Search Report dated Apr. 24, 2020 for the European Patent Application No. 19213718.0.

* cited by examiner

*Primary Examiner* — David Perlman
(74) *Attorney, Agent, or Firm* — Volpe Koenig (57) ABSTRACT

A method and apparatus for performing facial registration includes selecting a plurality of target locations for registration. It is indicated that registration is taking place at each of the plurality of target locations, and it is indicated that registration is complete at the each of the plurality of target locations as each target location is registered. Once the registration of all target locations is complete, it is indicated to the system.

20 Claims, 7 Drawing Sheets

METHOD AND APPARATUS FOR PERFORMING FACIAL REGISTRATION

SUMMARY

A method for performing a facial recognition is disclosed. The method includes selecting a plurality of target locations for registration. Registration takes place at each of the plurality of target locations, and is complete at each of the plurality of target locations as each target location is registered. Once the registration of all target locations is complete, it is indicated to the system.

A system for performing facial recognition is disclosed. The system includes a workstation, a display in communication with the workstation, a magnetic emitter located proximate to the face of a patient, and a registration probe in communication with the workstation. The registration probe includes an actuator and a magnetic wave receiver that receives a magnetic signal from the magnetic emitter to identify a location in space of the registration probe relative to the magnetic emitter. The registration probe indicates that registration is taking place at each of the plurality of target locations on a person's face, indicates that registration is complete at the each of the plurality of target locations as each target location is registered, and indicates that the facial registration of all target locations is complete.

A registration probe for performing facial recognition is disclosed. The registration probe includes a magnetic wave receiver that receives a magnetic signal from a magnetic emitter located proximate to the face of the patient to identify a location in space of the registration probe relative to the magnetic emitter, and an actuator. The registration probe indicates that registration is taking place at each of the plurality of target locations on a person's face, indicates that registration is complete at the each of the plurality of target locations as each target location is registered, and indicates that the facial registration of all target locations is complete.

BRIEF DESCRIPTION OF THE DRAWINGS

A more detailed understanding may be had from the following description, given by way of example in conjunction with the accompanying drawings wherein.

DETAILED DESCRIPTION

The present application is related to a method and apparatus for performing a facial recognition. In particular, the present application is directed to a method and apparatus for performing a facial recognition for an ear/nose/throat (ENT) procedure, such as a nasal dilation.

In general, a person typically has eight or so sinus openings, (e.g., the frontal, anterior ethmoidal, maxillary, and middle ethmoidal, for each side), although the number of openings varies from person to person. Each of those sinus openings include areas that are very small in diameter. Accordingly, when an opening becomes clogged for one reason or another, no drainage may occur from within the sinuses. In this case, problems can occur. For example, an accumulation of mucus can cause various health issues such as infections.

In order to treat these problems, a medical procedure such as sinus dilation may be used. Sinus dilation is a technique for increasing the size of the sinus passageway to provide a more unrestricted flow of fluids to alleviate sinus congestion. Sinus dilation is performed by using a tool that is inserted into the sinus cavity that includes a balloon which can be inflated. The balloon is inserted into the middle of the small sinus opening and dilated. This dilation applies pressure on the sinus opening to widen it (e.g., by reshaping the tissue structure of the sinus cavity). The opening remains at this increased size once the balloon is taken out, thus providing a larger passageway for fluid flow.

To perform the nasal dilation procedure, or any ENT procedure that is similar, it is important that the physician performing the procedure know the location of the tool within the nasal cavity with a great degree of accuracy. The physician views an image of the patient's nasal cavities on a display screen and navigates within the patient's actual cavities by manipulating the tool, while looking at an image of the location of the tool on the screen. Any inaccuracies regarding the location of the tool within a patient's nasal cavity may cause the physician to damage the nasal cavity and/or to perform the procedure in the wrong place within the cavity. Therefore, it is very important that the location of the tool on the screen coincides accurately to where the actual tool is within the actual nasal cavity of the patient.

In order to ensure that the physician knows, with accuracy, the location within the nasal cavity where he or she is performing the procedure, a registration procedure is performed. The registration procedure allows the physician to view the image that is on the display screen and register locations on a patient's face in that image. Although a system, apparatus and method are described in more detail below for performing a registration, briefly the image that is displayed, for example, is from a computerized tomography (CT) scan that is taken of the patient's head area prior to the ENT procedure. The registration is then performed by an operator, (e.g., physician or other technician), using a registration probe that is placed on various locations of a patient's face. Furthermore, the patient's head is situated in a magnetic field. The registration probe's location is registered on the CT scan that is displayed.

Conventional registration techniques include the operator touching the registration probe to different areas on the patient's face. However, conventional registration techniques do not provide a convenient way for the operator to connect and disconnect the registration probe at each location being registered as a target location, or to indicate when registration is complete.

Accordingly, described herein is a method, apparatus and system for performing a facial registration. The facial registration is performed by an operator who is able to connect and disconnect the registration tool from the registration system. In addition, the operator may indicate when the registration process is complete.

Figure 1:
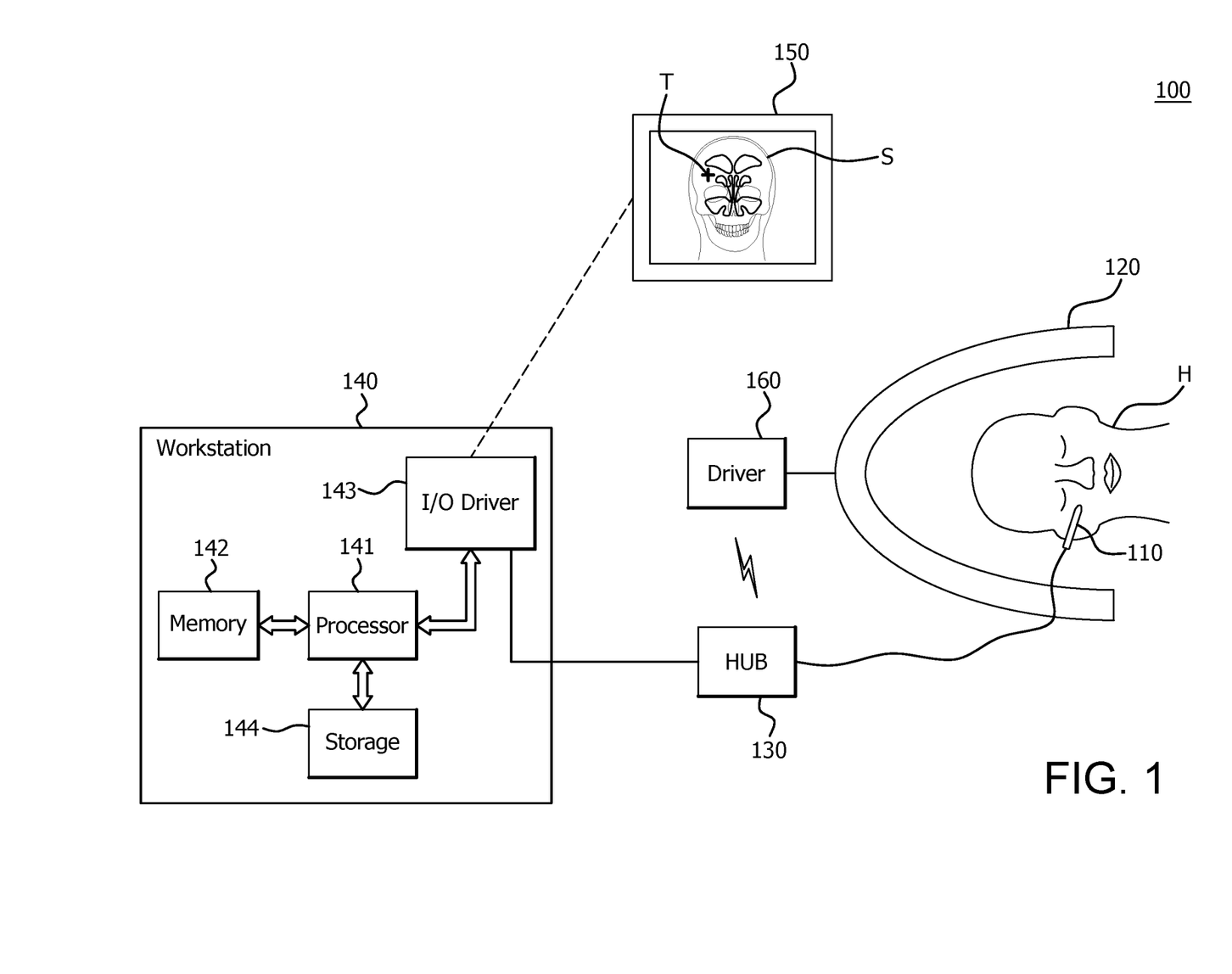
FIG. 1 is a diagram of an example system for performing a facial registration.

FIG. 1 is a diagram of an example system 100 for performing a facial registration. The system includes a registration probe 110, a magnetic field emitter 120, a hub 130, a workstation 140, a display 150, and a magnetic driver 160. The registration probe 110 and the magnetic field emitter 120 may also be connected to the hub 130 via the magnetic driver 160, which is connected to the workstation 140, and receives the signals from both the registration probe 110 and the magnetic emitter 120 to transfer to the workstation 140. However, the registration probe 110 and the magnetic driver 160 may be in direct communication with the workstation 140, exclusive of a signal traversing through the hub 130.

The workstation 140 includes, for example, a processor 141, a memory 142, an input/output (I/O) driver 143, and storage 144, which allow the workstation 140 to receive input data and output data via the I/O driver 143, and store data in the storage 144 and/or memory 143 as needed for processing. The workstation 140 is also connected to the display 150. The driver 160 is connected to the magnetic emitter 120 to emit one or more magnetic fields around a patient's head H. As can be seen on the display 150, an image S is displayed that has a target T on it. The target T indicates a current location of the registration probe 110 in space with respect to the patient's head H. An operator can then see the target on the image S and register areas of the patient's face on the image S for later use in an ENT procedure. It should be noted that the location of the magnetic field emitter 120 is shown for example purposes and the emitter 120 could be located in additional areas to provide a magnetic image. For example, a portion of the emitter 120 could be located beneath the patient's head H, and may include a plurality of magnetic field generators to increase the accuracy of the location. In the case where a plurality of field generators are utilized, the registration probe would be configured to register a plurality of magnetic fields.

To perform a registration, the registration probe 110 includes components to allow it to be accurately located with respect to the patient's head H, and more particularly to the patient's face.

Figure 2:
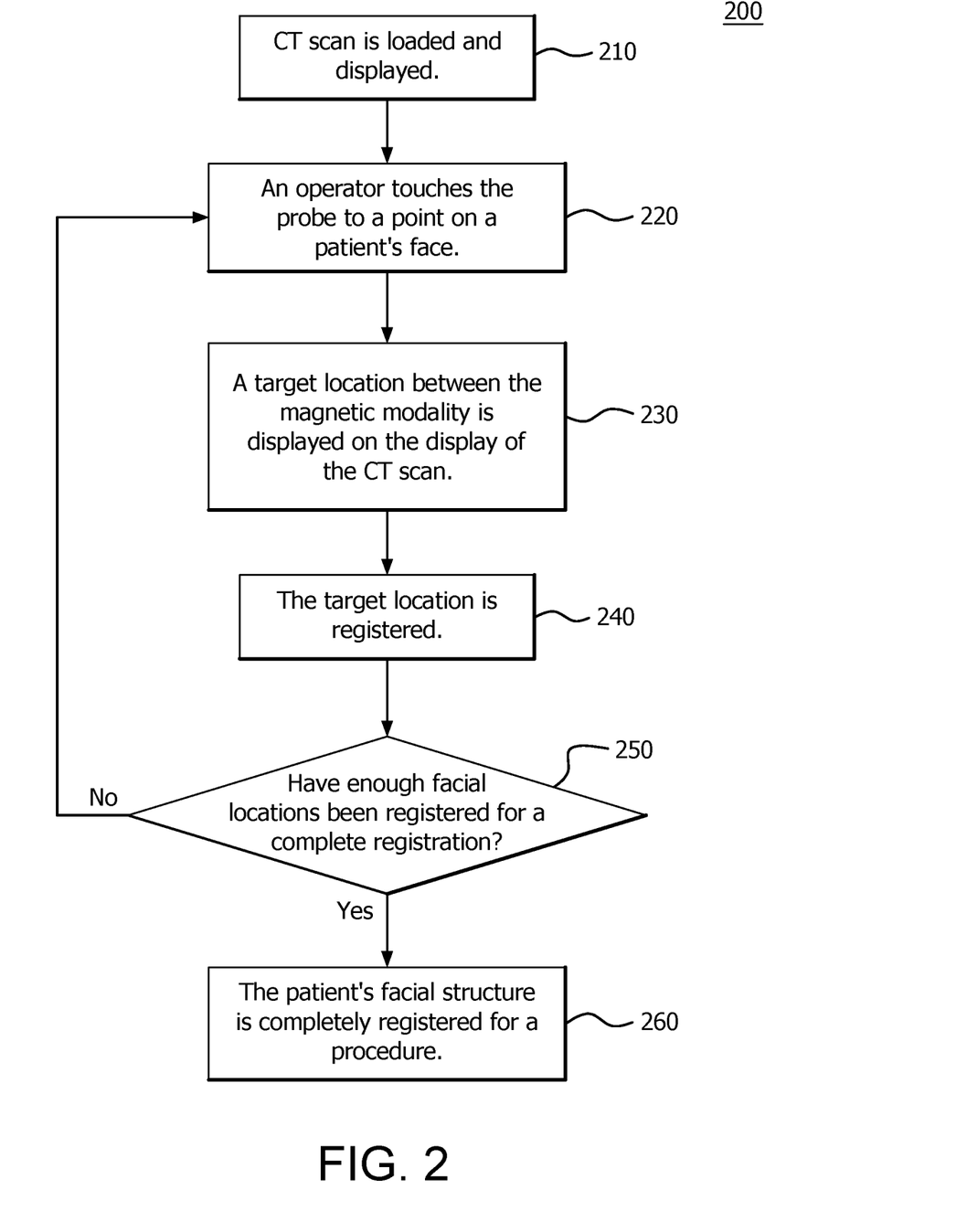
FIG. 2 is a flow diagram of an example conventional method for performing a facial registration.

FIG. 2 is a flow diagram of an example conventional method 200 for performing a facial registration. In step 210, a CT scan is loaded and displayed. For example, referring back to FIG. 1, a CT scan file that has been captured previously and loaded onto a memory device or electronically sent is loaded into the workstation 140 and displayed on the display 150 as image S.

Once the image is displayed, an operator touches the registration probe to a reference point on the patient's face to register that target location on the image (step 220). For example, the operator touches registration probe 110 to an area of the patient's face depicted in the display 150 of FIG. 1.

A target location between the magnetic modality is displayed on the CT scan (step 230). That is, the location that the coils 113 determine the registration probe 110 exists in three-dimensional space based on the magnetic field or fields received from the magnetic emitter 120 are displayed as a target location on the CT scan. This target location is then registered (step 240). This may be accomplished by the registration probe 110 transmitting its location information to the workstation 140 based on the detected magnetic fields by the coils 113, where the workstation 140 processes the location and determines where to overlay the location on the displayed image.

If enough facial locations have been registered for a complete registration (step 250), then the patient's facial structure is completely registered for the conventional procedure (step 260). If there are not enough locations registered in step 250, then the method returns to step 220, where the operator continues to touch other areas of the patient's face in order to cover a significant enough portion of the patient's face to completely register the patient's face for the ENT procedure.

Figure 3:
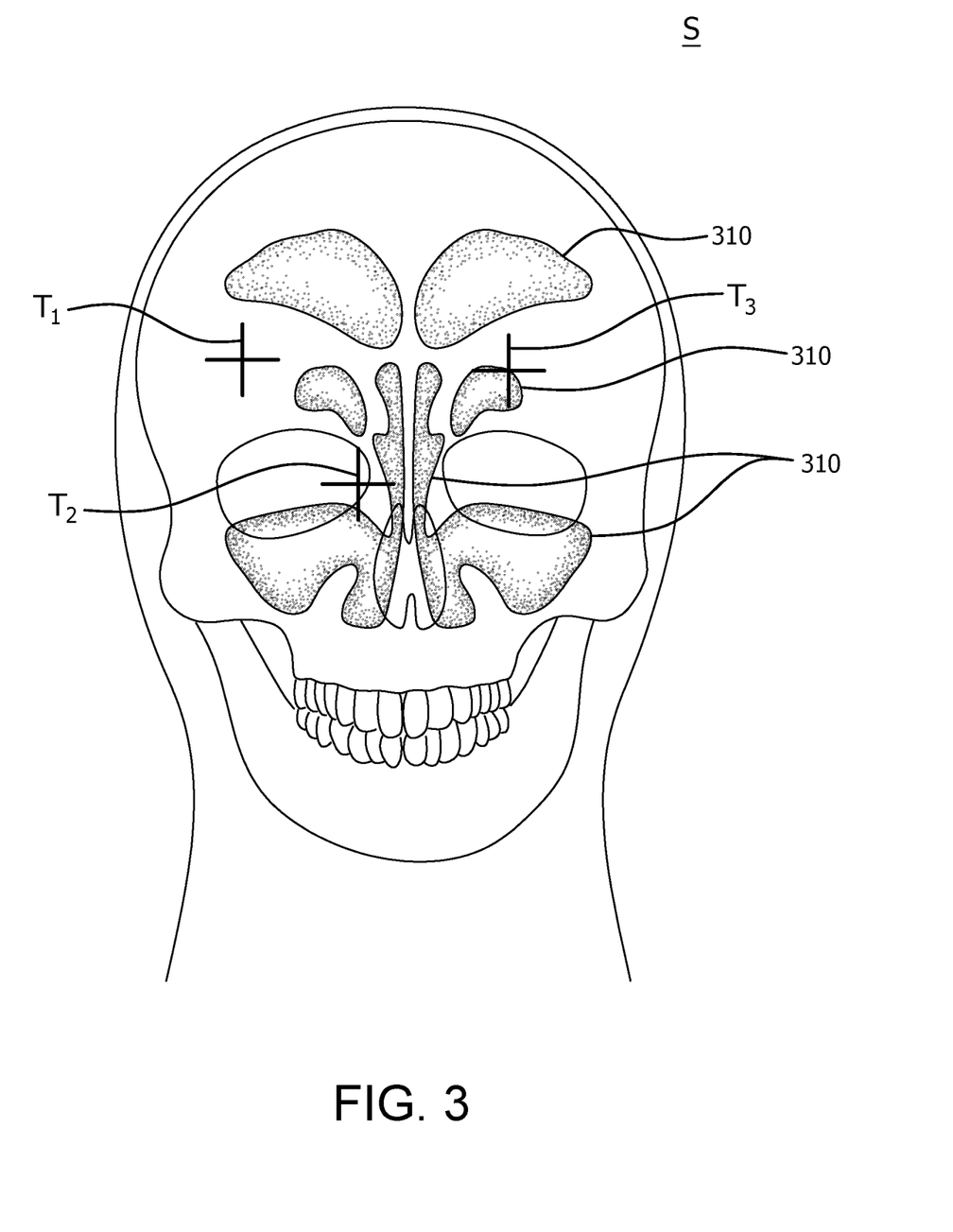
FIG. 3 is an example facial image for use during the facial registration method of FIG. 2.

FIG. 3 is an example facial image for use during the facial registration method of FIG. 2. For purposes of example, the facial image in FIG. 3 may be image S from FIG. 1. As can be seen in FIG. 3, targets T (designated $T_1$, $T_2$, and $T_3$) are shown as solid crosshairs. Referring back to step 220 of method 200, Target $T_1$ corresponds to a first point on the patient's face touched by the operator, target $T_2$ corresponds to a second point on the patient's face touched by the operator, and target $T_3$ corresponds to a third point on the patient's face touched by the operator. A number of nasal cavities 310 can also be seen in the image S as depicted in FIG. 3.

However, it would be beneficial in having an enhanced registration capability by providing the physician the ability to indicate when a target on the patient's face is being touched, (e.g., by clicking and releasing a button), and when registration is complete and no further targets on a patient's face will be registered. In addition, physicians work with a number of devices when performing an ENT procedure and it would be beneficial to provide an improved an actuation device that signals to the system 100 that a particular tool, (e.g., registration probe suction tool, pointer, blade, navigation device, ultrasonic tip or other interchangeable probe), is being connected or disconnected to the system 100.

Figure 4A:
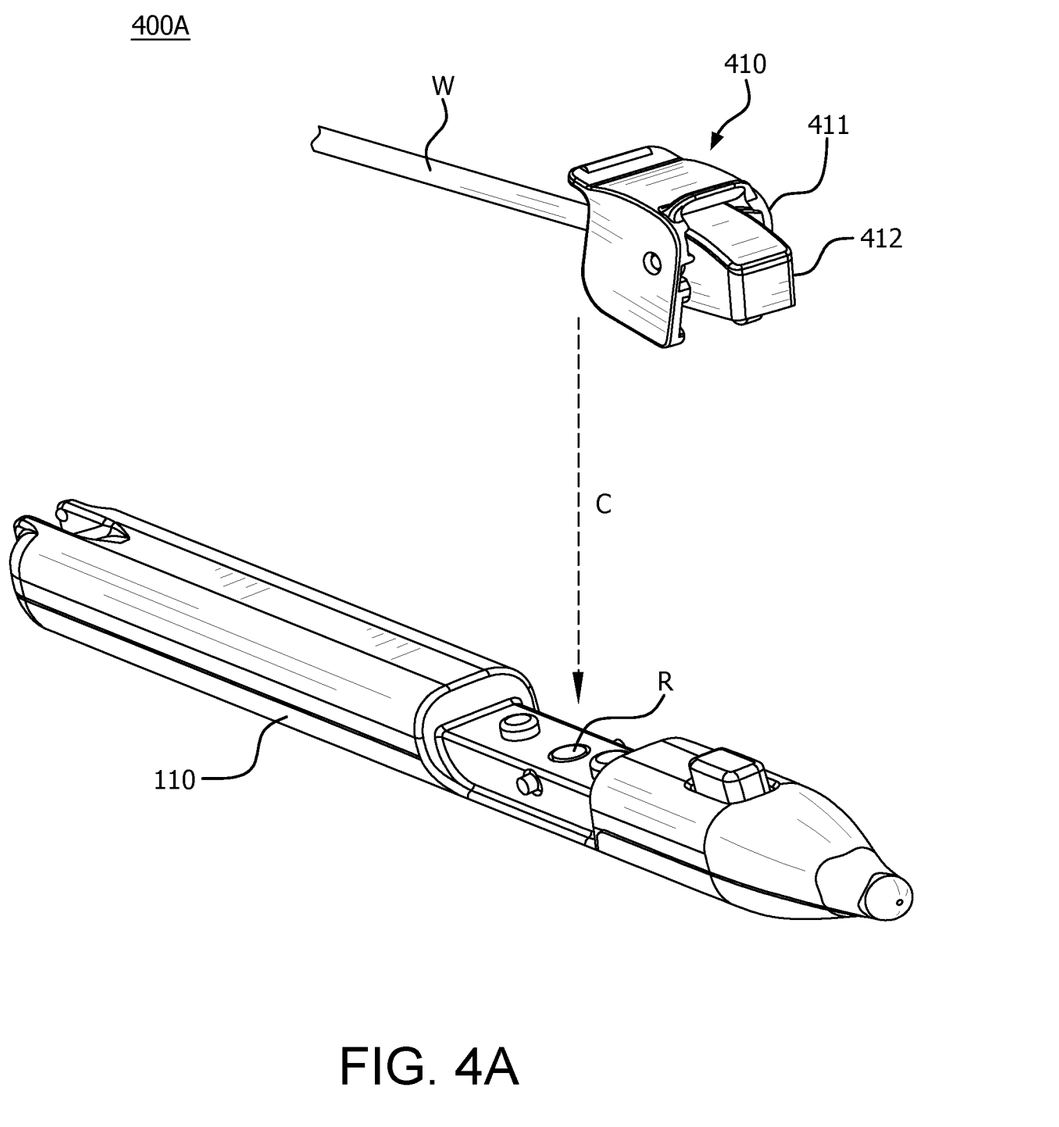
FIG. 4A is a diagram of an example registration probe and example registration actuation device for use in the system of FIG. 1.
Figure 4B:
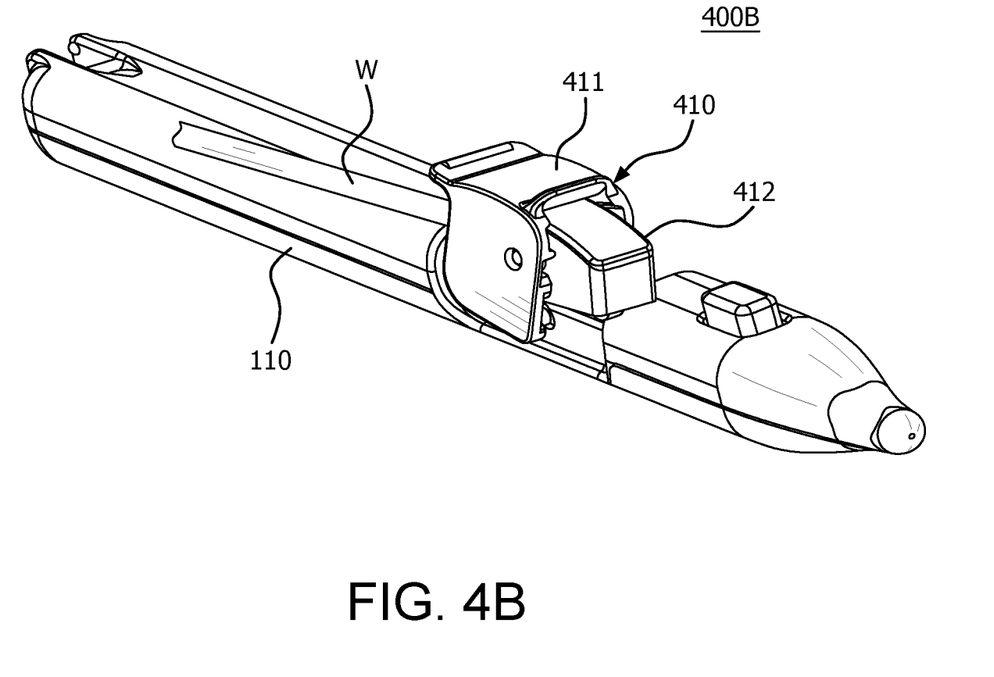
FIG. 4B is a diagram of the example registration probe and example registration actuation device of FIG. 4A connected together.

FIG. 4A is a diagram 400A of an example registration probe 110 and an example registration actuation device 410 for use in the system of FIG. 1. FIG. 4B is a diagram 400B of the example registration probe 110 and example registration actuation device 410 of FIG. 4A connected together. The registration probe 110 includes a recessed area including a registration activation button R, which activates the components in the registration probe 110, (e.g., coils that receive the magnetic fields emitted by the emitter 120).

Continuing to refer to FIGS. 4A and 4B, the registration activation device 410 includes a connector 411 and a sensor unit 412. A wire W connects the device 410 to the workstation 140, (e.g., via the hub 130) to transmit data to and from the device 410 and workstation 140. The device 410 is placed on the registration probe 110 along the arrow C to attach it to the registration probe 110. The connected registration probe 110 and registration activation device 410 are shown in FIG. 4B.

Figure 5:
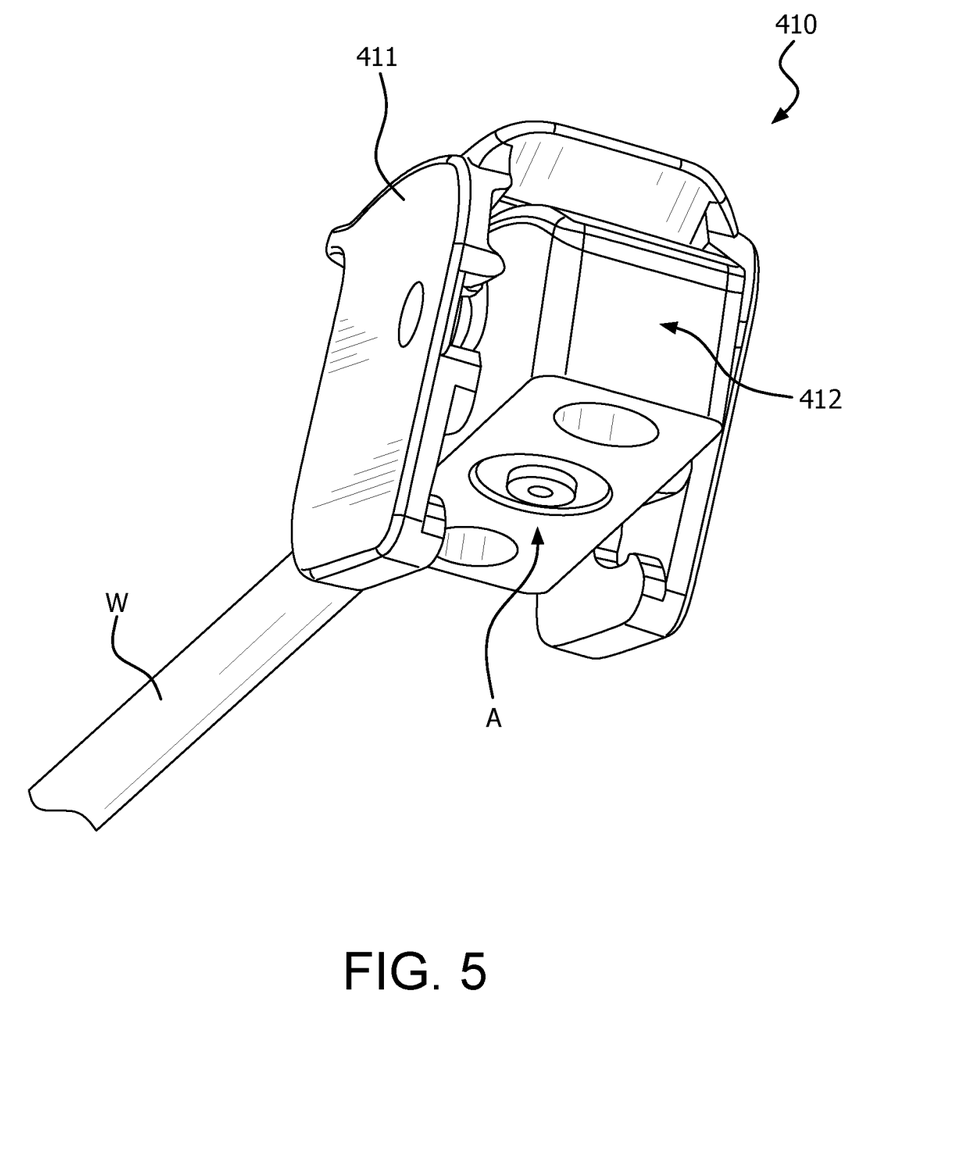
FIG. 5 is an underneath perspective view of the registration actuation device of FIGS. 4A and 4B.

FIG. 5 is a bottom perspective view of the registration actuation device 410 of FIGS. 4A and 4B. As shown in FIG. 5, the bottom of the sensor unit 412 includes an actuator A. Actuator A coincides with the registration activation button R such that when the connector 411 is depressed, actuator A activates activation button R as well as causes a signal to be transmitted to the workstation 140 along wire W for use in the method described below.

Figure 6:
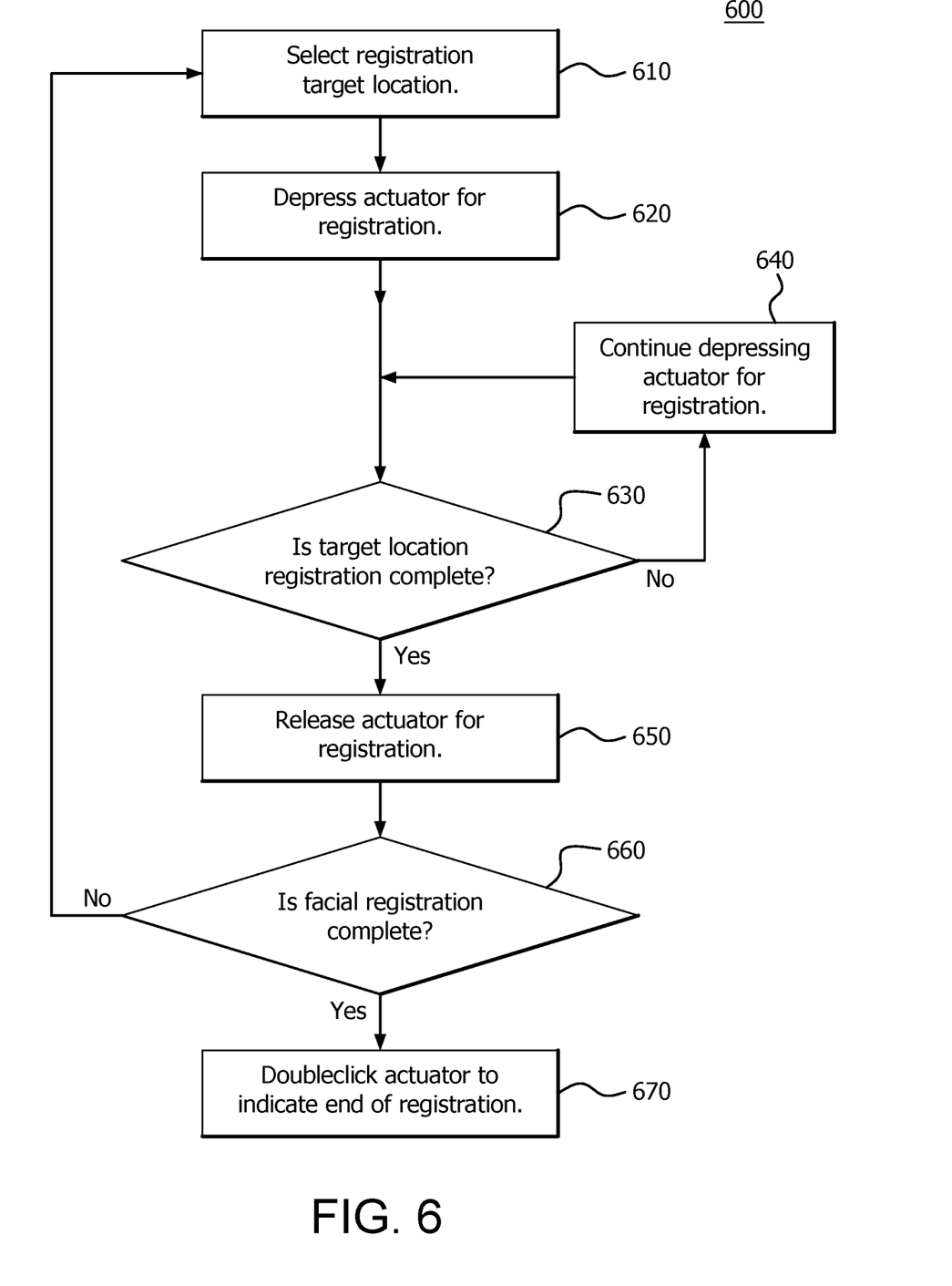
FIG. 6 is a flow diagram of an example method for performing a facial registration with example registration probe and example registration actuation device of FIGS. 4A and 4B.

FIG. 6 is a flow diagram of an example method 600 for performing a facial registration with example registration probe 110 and example registration actuation device 410 of FIGS. 4A and 4B. In step 610, the operator selects a registration target location and touches the patient's face at that target location. For example, referring back to FIG. 3, the operator may select target location $T_1$ for registration. The operator then depresses the actuator, (e.g., actuator A of device 410), in step 620, which indicates to the system 100 that the location $T_1$ is being registered as a target location. If the target location registration is not complete (step 630), then the operator continues to depress the actuator until the registration is complete for that target location (step 640).

If the registration at that target location is complete (step 630), then the operator releases the actuator (step 650), which indicates to the system 100 that registration in that target location has been registered. In step 660 then, it is determined if the facial recognition is completed. If it is not, then the method reverts to step 610, where additional target locations are registered, (e.g., $T_2$, $T_3$, and so forth). If the facial registration is complete in step 660, then the operator indicates the end of registration (step 670), such as by double-clicking the actuator, for example.

It should be noted that the method, apparatus and system described above can include additional modifications. For example, the registration probe, (e.g., registration probe 110), as well as other components in the system in communication with one another may be in wired or wireless communication. That is, transceivers and antennas may be included in the devices, (e.g., registration probe 110 and other components of system 100), that can transmit and receive data wirelessly to one another. It should also be noted that the registration actuation device 410 can be utilized to signal to the system 100 that a tool, such as described above, is being connected or disconnected to the system by utilizing the actuator A.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for performing facial registration using a registration probe, comprising:
   selecting a plurality of target locations for registration;
   indicating, during a first registration mode, with the registration probe by an operator of the registration probe, using a first indication notification that registration is taking place at a single target location of each of the plurality of target locations;
   indicating, during the first registration mode, with the registration probe by the operator of the registration probe using a second indication notification, that registration is complete at each single target location of the plurality of target locations as each single target location is registered; and
   indicating, during the first registration mode, with the registration probe by the operator of the registration probe, using a third indication notification that the facial registration of all target locations of the plurality of target locations is complete, wherein the third indication notification is different from the first indication notification and the second indication notification.

2. The method of claim 1 wherein the indicating that registration is to take place at each of the plurality of target locations includes depressing an actuator on the registration probe.

3. The method of claim 2 wherein the indicating that registration is complete at the each of the plurality of target locations as each target location is registered includes releasing the actuator.

4. The method of claim 1 wherein the indicating that the facial registration of all target locations is complete includes multiple depressing of an actuator.

5. The method of claim 1 wherein upon indicating that registration is complete at one of the plurality of target locations, the target location is registered on a computerized tomography (CT) scan.

6. The method of claim 5 wherein upon indicating that the facial registration of all target locations is complete, all target locations are registered.

7. A system for performing facial recognition, comprising:
   a workstation;
   a display in communication with the workstation;
   a magnetic emitter located proximate to the face of a patient; and
   a registration probe in communication with the workstation, the registration probe including an actuator and a magnetic wave receiver that receives a magnetic signal from the magnetic emitter to identify a location in space of the registration probe relative to the magnetic emitter, the registration probe configured to:
      indicate, during a first registration mode, by an operator of the registration probe using a first indication notification, that registration is taking place at a single target location of each of the plurality of target locations on a person's face;
      indicate, during the first registration mode, by the operator of the registration probe using a second indication notification, that registration is complete at each single target location of the plurality of target locations as each target location is registered; and
      indicate, during the first registration mode, by the operator of the registration probe using a third indication notification, that the facial registration of all target locations of the plurality of target locations is complete, wherein the third indication notification is different from the first indication notification and the second indication notification.

8. The system of claim 7 wherein the workstation transmits the correlated target locations to the display for display on the reference image of the face of the patient.

9. The system of claim 8 wherein the reference image is a computerized tomography (CT) scan of the face of the patient.

10. The system of claim 7 wherein the registration probe and the workstation are in wireless communication with one another.

11. The system of claim 7, further comprising a hub device in communication with the registration probe and the workstation for effectuating communication between the registration probe and the workstation.

12. The system of claim 11 wherein the hub is in communication with a driver that drives the magnetic emitter.

13. The system of claim 7 wherein the workstation further comprises a processor, a memory and a storage component in communication with one another, and wherein a reference image is stored in the memory of the workstation for transmission to the display.

14. The system of claim 7 wherein the magnetic receiver is a coil disposed in the registration probe for receiving the magnetic wave.

15. The system of claim 7 wherein the registration probe is configured to indicate that registration is taking place at each of the plurality of target locations on a person's face when the actuator is depressed.

16. The system of claim 15 wherein the registration probe is configured to indicate that registration is complete at the each of the plurality of target locations as each target location is registered when the actuator is released.

17. The system of claim 7 wherein the registration probe is configured to indicate that the facial registration of all target locations is complete when the actuator is depressed multiple times.

18. A registration probe in communication with a facial recognition system, comprising:
a magnetic wave receiver that receives a magnetic signal from a magnetic emitter located proximate to the face of the patient to identify a location in space of the registration probe relative to the magnetic emitter; and
an actuator,
wherein the registration probe is configured to:
indicate, during a first registration mode, by an operator of the registration probe using a first indication notification, that registration is taking place at a single target location of each of the plurality of target locations on a person's face;
indicate, during the first registration mode, by the operator of the registration probe using a second indication notification, that registration is complete at each single target location of the plurality of target locations as each target location is registered; and
indicate, during the first registration mode, by the operator of the registration probe using a third indication notification, that the facial registration of all target locations of the plurality of target locations is complete, wherein the third indication notification is different from the first indication notification and the second indication notification.

19. The registration probe of claim 18 wherein the registration probe is configured to indicate that registration is taking place at each of the plurality of target locations on a person's face when the actuator is depressed, and that registration is complete at the each of the plurality of target locations as each target location is registered when the actuator is released.

20. The registration probe of claim 18 wherein the registration probe is configured to indicate that the facial registration of all target locations is complete when the actuator is depressed multiple times.

* * * * *